United States Patent [19]

Arechaga et al.

[11] Patent Number: 4,690,945

[45] Date of Patent: Sep. 1, 1987

[54] PROCESS FOR THE PREPARATION OF 5'-SUBSTITUTED 2-(3'-THIENYL)PROPIONIC ACIDS

[75] Inventors: Sabastian J. Arechaga; Jose O. O. Granell; Carmen S. Linan; Alfonso P. Vallejo; Jose A. P. Gabarro, all of Barcelona, Spain

[73] Assignee: Laboratorios Madaus Cerafarm, S.A., Barcelona, Spain

[21] Appl. No.: 818,798

[22] Filed: Jan. 14, 1986

Related U.S. Application Data

[63] Continuation of Ser. No. 697,431, Feb. 1, 1985, abandoned, which is a continuation of Ser. No. 505,061, Jun. 16, 1983, abandoned, which is a continuation-in-part of Ser. No. 405,655, Aug. 5, 1982, abandoned.

[30] Foreign Application Priority Data

Aug. 11, 1981 [ES] Spain ..................................... 504690

[51] Int. Cl.⁴ ..................... A61K 31/38; C07D 333/22; C07D 333/24
[52] U.S. Cl. .................................... 514/448; 514/438; 549/72; 549/79
[58] Field of Search ..................... 549/72, 79; 514/448, 514/438

[56] References Cited

U.S. PATENT DOCUMENTS 4,159,986 7/1979 Clemence ............................ 549/72

OTHER PUBLICATIONS

Wagner, Syn. Org. Chem. 1965, pp. 426–429.

Primary Examiner—Alan Siegel
Attorney, Agent, or Firm—Felfe & Lynch

[57] ABSTRACT

The present invention relates to the preparation of compounds, useful in animals and in humans, as nonsteroid anti-inflammatory agents of the formula

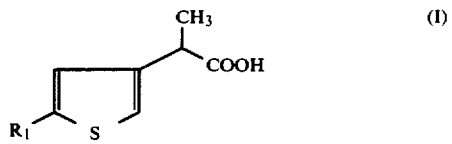

(I)

in which $R_1$ is hydrogen, alkyl, alkanoyl, phenylalkyl or phenylalkanoyl, said alkyl and alkanoyl groups having 1 to 6 carbon atoms and said phenyl group having 1 to 3 halogen substituents or 1 to 3 alkyl or alkoxy substituents, said alkyl or alkoxy substituents having 1 to 4 carbon atoms, and their pharmaceutically acceptable salts.

5 Claims, No Drawings

PROCESS FOR THE PREPARATION OF 5'-SUBSTITUTED 2-(3'-THIENYL)PROPIONIC ACIDS

This is a continuation of Ser. No. 697,431, filed Feb. 1, 1985 now abandoned, which is a continuation of Ser. No. 505,061, filed June 16, 1983 now abandoned, which is a continuation-in-part of Ser. No. 405,655, filed Aug. 5, 1982 now abandoned.

BACKGROUND

Preferred compounds of the present invention are compounds of Formula I wherein $R_1$ is isobutyl, benzyl, isobutyryl, benzoyl, 4-chlorobenzoyl, 4-methylbenzoyl or 2,4-dichlorobenzoyl, or any pharmaceutically acceptable salt of same, such as salts formed by nontoxic metal cations (for example, sodium, lithium, potassium, magnesium) or those formed with nontoxic organic bases of the amine type (ethanolamine, triethanolamine, lysine, etc.).

The process that is the subject of the present invention is characterized by the following scheme:

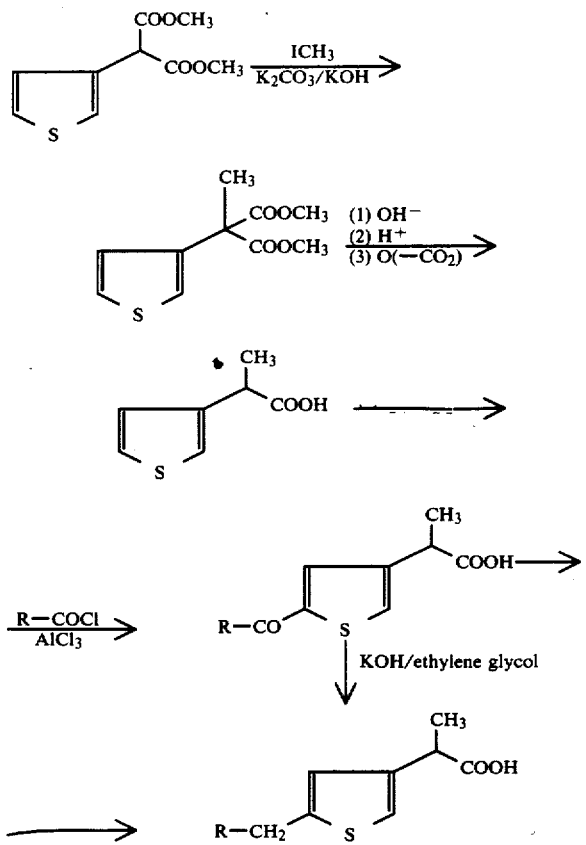

This process is characterized by using a 2-(3'-thienyl)-malonic ester, preferably dimethyl-2-(3'-thienyl)malonate or diethyl-2-(3'-thienyl)malonate as raw material which, in a first step, is treated with methyl iodide for the purpose of methylating the CH group. The reaction is performed under solid-to-liquid phase transfer conditions, using as solid bases a mixture of potassium carbonate and potassium hydroxide. The organic solvent can be toluene, benzene or any solvent of low polarity, preferably the first mentioned. As the phase transfer catalyst any quaternary ammonium salt can be used that is suitable for this purpose, preferably tetrabutylammonium acid sulfate (TBAB).

In a second step the process consists in the hydrolysis of 2-methyl-2-(3'-thienyl)malonic ester by the conventional method, i.e., by refluxing the compound in a solution of potassium hydroxide in ethanol. During this process, partial decarboxylation of one of the carboxyl groups of the resultant 2-(3'-thienyl)malonic acid can also occur, which is isolated by conventional methods. The product of the hydrolysis is subjected, without preliminary treatment, to decarboxylation by heating in a vacuum of the order of 20 mm of mercury. Afterward, it is purified by vacuum distillation and the corresponding 2-3'-thienyl)propionic acid is obtained.

In a third step, this acid is treated with an appropriate acid chloride (e.g., isobutyryl chloride, benzoyl chloride, etc) under Friedel-Crafts conditions, i.e., in the presence of a Lewis acid type catalyst, preferably aluminum trichloride, in a suitable organic solvent such as methylene chloride, carbon sulfide, etc. After the treatment commonly practiced in this type of reactions, a raw product is arrived at which is thoroughly purified by crystallization, or by silica gel column chromatography, or by any of the methods commonly used in organic synthesis. In this manner the corresponding 2-(5'-acyl-3'-thienyl)propionic acids, which are the subject of the present invention, are obtained.

From these acyl compounds, the 2-(5'-alkyl-3'-thienyl)propionic acids, and 2-(5'-phenylalkyl-3'-thienyl)propionic acid compounds which are also subject matter of the present invention, can be obtained from those above by the Wolf-Kishner process, i.e., by prolonged boiling of the 2-(5'-acyl-3'-thienyl)-propionic acids in the presence of potassium hydroxide and ethylene glycol. After the treatment conventionally practiced in this type of reaction, the final product is purified by high-vacuum distillation or by column chromatography on silica.

The compounds of the present invention, especially 2-5'-benzoyl-3'-thienyl)propionic acid (I) and 2-(5'-(4''-chlorobenzoyl)-3'-thienyl)propionic acid (II), have an anti-inflammatory activity in mammals, and therefore they are useful in the treatment of arthritis, rheumatism, and other inflammatory type diseases.

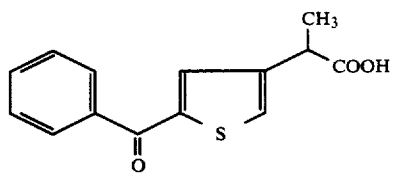

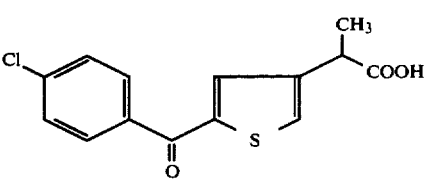

The pharmacological tests were performed on rats and mice, using the carrageenin edema procedure on rats' legs and backs by the test for anti-inflammatory action and the acetic acid contorsion and hot plate tests on mice for the purpose of testing analgesic action.

In the anti-inflammatory action test, the test was performed on rat leg edema induced by carrageenin, administering the compounds per os and measuring the volume of the edema 3 hours later by plethysmography.

The anti-inflammatory action of these compounds was also examined by the carrageenin abscess test on rats' backs, the abscess being weighed 24 hours after administration of the product.

The results obtained in both tests are expressed as a percentage of inhibition of the edema or abscess, and were better than 30% in comparison with a control group.

For the examination of analgesic action, the acetic acid and hot plate tests were used.

In both tests the analgesic activity of these compounds is evaluated by the greater or lesser degree of inhibition of the chemical or thermal pain stimulus.

In the acetic acid test, the number of contorsions (stretching) is determined, which are produced for 30 minutes following intraperitoneal administration of dilute acetic acid. Analgesic action is also tested by the hot plate test in which the pain stimulus is thermal, the time being measured in seconds which the animal takes to respond to the stimulus by licking its feet.

The results obtained in both test, in harmony with the anti-inflammatory action tests, shows that these compounds, especially I and II, have an analgesic action.

The pharmacological action of all these compounds is manifested in oral and parenteral administration, although it is also evident in rectal and topical or local administration.

The dosages can vary from minimums of 6.25 mg/kg to maximums of 100 mg/kg. However, these are very far from the $LD_{50}$ (400 to 1500 mg/kg), and yet they have ample therapeutic indications.

The greater or lesser intensity of action depends on the radical $R_1$, the benzoyl radical being the one of greatest activity. Also, the presence or absence of halogen radicals in the benzoyl group has an influence. This is shown by the good results obtained with compound I and by its low median effective dose ($ED_{50}$), which confirms its notable analgesic and anti-inflammatory action. As for its monohalogenated derivative II, it too has a notable pharmacological action, though it is inferior to that of compound I.

The rest of the compounds tested have a variable action of a fugitive character, compound IV (Example 7) being the best representative of this action due to its great similarity to compound II, which confirms the superiority of the benzoyl radical over others (isobutyl, for example).

In man, the usual daily dose of these compounds, preferably compounds I and II, can vary from 0.5 mg to 25 mg per kilogram, t.i.d., averaging 10 mg/kg.

Therefore, the process of the present invention serves for obtaining, preferentially, the two compounds A and B of the formulae

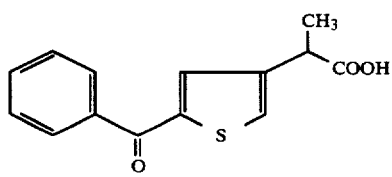

and

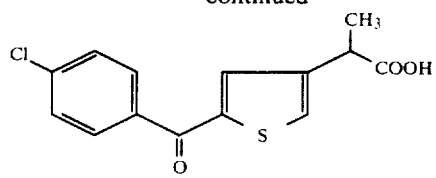

whose potent anti-inflammatory activity can make them useful anti-inflammatory agents.

The following examples are set forth by way of explanation without thereby limiting the invention:

EXAMPLE 1

Preparation of 2-methyl-2-(3'-thienyl)methyl malonate 44.9 g (0.21 moles as ethyl ester) of 2-(3'-thienyl)methylmalonate, 31.8 g (0.23 mol) of anhydrous $K_2CO_3$ and 500 ml of distilled benzene are placed in a one-liter, three-mouthed balloon flask provided with reflux coolant, mechanical agitation and an addition funnel. The mixture is thoroughly agitated, and 12.65 g (0.23 mol) of KOH 85%, perfectly pulverized, is carefully added. The resultant suspension is heated, slowly at first, and then refluxed, it being observed that stirring becomes more difficult, until a viscous paste is obtained (10 minutes of refluxing). The paste is allowed to cool and 1.56 g of tetrabutylammonium bisulfate (0.0045 mol) is added and, drop by drop with vigorous agitation, 47.0 g (0.33 mol) of methyl iodide, over a period of 15 minutes. While this last reagent is being added, a considerable fluidification of the reaction mixture is observed. Then the mixture is heated (bath at 60° C.) for 7 hours.

Then it is cooled and filtered and the benzene phase is removed with a rotary evaporator, a crude product of 43.8 g being obtained (0.171 mol, approx. 83%) which is not purified.

IR (film) 3110, 2980, 2950, 2900, 1740, 1540, 1460, 1375, 1260, 1220, 1180, 1100, 1010, 860, 780 cm$^{-1}$.

NMR (Cl$_4$C): 7.05–7.20 ppm compound (3) H thiophene, 4.08 c (2.6) CH$_2$ ethyl ester, 3.72 s (3) methyl ester, 1.78 s (3) methyl, 1.18 t (4.0) ethyl ester.

EXAMPLE 2

2-(3'-thienyl)propionic acid

In a 250 ml balloon, 42.0 g of the product obtained in Example 1 is placed, plus 27.0 g (0.110 mol) of KOH in pellets, 68 ml of ethanol, and 34 ml of water, and the mixture is refluxed for 4 hours. Then it is allowed to cool and all the alcohol is removed with a rotary evaporator. Water is added, and the mixture is acidified to pH=1 with concentrated HCl, with external cooling by water. At the end of a certain amount of time, a yellowish solid precippitates, which is the crude 2-methyl-2-(3'-thienyl)malonic acid. In a vacuum distillation apparatus, 24.0 g of this crude product is placed, and heated in a silicone bath at 180° C. Once the solid melts, an abundant release of $CO_2$ is noted. When this diminishes, a vacuum of 25 torr is applied to the system for half an hour. The mixture is cooled and the resultant oil is vacuum distilled, producing 16.87 g (0.108 mol, 90%) of slightly yellowish oil.

B.P.=115°–115° at 0.10 torr.

IR (film): 3600–2200, 1710, 1530, 1460, 1415, 1375, 1230, 1150, 910, 760, 665 cm$^{-1}$.

EXAMPLE 3

Friedel-Crafts reaction between 2-(3'-thienyl)propionic acid and various acid chlorides. General procedure.

In the preparation of each compound, the following procedure is used: In a three-mouthed balloon equipped with a magnetic stirrer, calcium chloride tube and an addition funnel, 2.5 mol of anhydrous $AlCl_3$, thoroughly pulverized and suspended in 500 ml of dry methylene chloride, and the mixture is externally cooled with a bath at 0° C. 1 mol of acid obtained in Example 2 is added. After cooling, 1 mol of acid chloride are added slowly through the addition tube, considered as dissolved in 3000 ml of dry methylene chloride. After this addition is completed, another 2000 ml of methylene chloride is added and stirred at 0° C. for the amount of time indicated. Hydrolysis is performed by pouring the cold reaction mixture onto sufficient water. It is thoroughly extracted with methylene chloride, and then the organic phase is extracted with a dilute solution of NaOH followed by acidification of the aqueous layer and extraction with methylene chloride, drying and elimination of the solvent. The crude product obtained is subjected to further purification (see later examples).

EXAMPLE 4

Preparation of 2-(5'-benzoyl-3'-thienyl)propionic acid (I)

Following the method described in Example 3, the following amounts are used:
22.0 g (160.4 mmol) of $AlCl_3$, 65 ml. $CH_2Cl_2$
9.1 g (64.1 mmol) of benzoyl chloride
10.0 g (64.1 mmol) of 2-(3'-thienyl)propionic acid
300 ml of $CH_2Cl_2$.
Reaction time: 3 hours.
The crude product obtained is crushed with hexane.
Yield: 65%.
NMR ($CD_3COCD_3$): 8.30 (wide) H acid, 7.00–7.35 comp (3) H thiophenic, 3.70 c (1) (I=7 Hz) H methinic, 1.33 d (3) (I=7 Hz) H methylic.

| Elemental Analysis ($C_7H_8O_2S$): | | |
|---|---|---|
| | Calculated | Found |
| C | 53.85% | 53.56% |
| H | 5.20% | 5.19% |
| S | 20.51% | 20.58% |

EXAMPLE 5

Preparation of 2-(5'-(4''-chloro)benzoyl-3'-thienyl)propionic acid (II)

Following the method of Example 3, the following quantities are used:
6.00 g of the starting acid (38.2 mmol)
6.72 g (38.2 mmol) of 4-chlorobenzoyl chloride
12.81 g (96.0 mmol) $AlCl_3$
210 ml of $CH_2Cl_2$.
Reaction time: 4 hours.
The crude product obtained by the reaction is purified by column chromatography, using Merck $SiO_2$ (silica gel 60, grain size 0.063–0.200 mm) and a mixture of benzene, ethyl acetate and acetic acid in a ratio of 85:7:8 as eluent.
The $R_F$ of the product is approximately 0.20.
Yield: 85%.

Melting Point: 66°–68° C.
IR (KBr): 3110, 3300, 2200, 1705, 1640, 1535, 1450, 1420, 1285, 1250, 1120, 925, 880, 710 cm$^{-1}$.
NMR ($CD_3COCD_3$): 7.95–7.50 ppm comp (7) H aromatic, 3.89 c (1) H methinic, 1.46 d (3) H methylic.

| Elemental Analysis ($C_{14}H_{12}O_3S$): | | |
|---|---|---|
| | Calculated | Found |
| C | 64.62% | 63.34% |
| H | 4.62% | 4.66% |
| S | 12.31% | 12.46% |

EXAMPLE 6

Preparation of 2-(5'-(2'',4''-dichloro)benzoyl-3'-thienyl)propionic acid (III)

Following the method of Example 3, the following quantities are used:
7.00 g (44.9 mmol) of the starting acid
9.41 g (44.9 mmol) of 2,4-dichlorobenzoyl chloride
14.97 g (110 mmol) of $AlCl_3$
300 ml. of $CH_2Cl_2$
Reaction time: 4 hours.
The crude product is purified by column chromatography using 600 g of $SiO_2$, and the same eluent as described in Example 4.
A clear, semi-solid oil is obtained weighing 8.85 g (30.0 mmol, 78%), which upon treatment with hexane quickly solidifies giving a whitish solid.
M.P.=112°–114° C.
IR (KBr): 3300–2200, 3100, 2990, 2940, 1715, 1645, 1595, 1420, 1310, 1295, 1240, 1200, 1120, 1090, 935, 855, 780, 750, 670 cm$^{-1}$.
NMR ($CD_3COCD_3$): 1.46 d (3) H methylic, 3.88 c (1) H methinic, 7.5–7.88 comp (5) H benzenic and thiophenic, 9.3 wide (1) H carboxylic.

| Elemental Analysis ($C_{14}H_{11}ClO_3S$): | | |
|---|---|---|
| | Calculated | Found |
| C | 51.06% | 50.85% |
| H | 3.04% | 3.14% |
| S | 9.73% | 9.69% |
| Cl | 21.58% | 21.42% |

EXAMPLE 7

Preparation of 2-5'-(4''-methyl)benzoyl-3'-thienyl)propionic acid (IV)

The method of Example 3 is followed, using the following amounts:
4.00 g (25.6 mmol) of the starting acid
3.96 g (25.6 mmol) of 4-methylbenzoic acid chloride
8.54 g (64 mmol) of $AlCl_3$
60 ml of $CH_2Cl_2$.
Reaction time: 3 hours.
The oily product is treated with hexane, and an ivory colored solid is obtained which weighs 3.99 g (14.6 mmol, 57%); it is purified by column chromatography, using a column of 30 mm diameter and 100 g of $SiO_2$.
M.P.=104°–107° C.
IR (KBr): 3300–2200, 3110, 2990, 2940, 1715, 1640, 1615, 1420, 1315, 1300, 1285, 1245, 1200, 1185, 1120, 935, 840, 785, 750, 670 cm$^{-1}$.

NMR (CD$_3$COCD$_3$): 1.46 d (3) H methyl, 2.41 s (3) H methylthiophenic, 3.92 c (1) H methinic, 7.3–7.8 comp (6) H thiophenic and benzenic, 7.0–9.6 wide (1) H carboxylic.

| Elemental Analysis (C$_{15}$H$_{14}$O$_3$S): | | |
|---|---|---|
| | Calculated | Found |
| C | 65.69% | 65.42% |
| H | 5.11% | 5.25% |
| S | 11.68% | 11.56% |

EXAMPLE 8

Preparation of 2-(5'-isobutyryl-3'-thienyl)propionic acid (V)

The general procedure of Example 3 is used, but with the following reagents and quantities:
34.0 g (0.253 mol) AlCl$_3$
15.71 g (0.101 mol) 2-(3'-thienyl)propionic acid
10.72 g (0.101 mol) of isobutyryl chloride
350 ml of CH$_2$Cl$_2$.

Reaction temperature: 0° C.
Addition over a period of 2 hours.
Reaction for 1 hour.

A crude product is obtained of 20.27 g, which is purified as in the foregoing examples by column chromatography, 17 g being recovered.

Yield: 74%.

IR (film): 3700–3300, 2980, 1710, 1660, 1420, 1200 cm$^{-1}$.

NMR (CD$_3$COCD$_3$): 8.02 s (1) wide, vanishes upon deuteration, 7.83 d (1) H thiophenic in position 2, 7.60 d (1) H thiophenic in position 4, 3.92 c (1) CH$_3$—CH—COOH, 3.48 m (1) (CH$_3$)$_2$CH—CO—, 1.53 d (3) C$\overline{H}_3$—CH—COOH, 1.20 d (6) (C$\overline{H}_3$)$_2$—CH—CO—.

| Elemental Analysis (C$_{11}$H$_{14}$O$_3$S): | | |
|---|---|---|
| | Calculated | Found |
| C | 58.39% | 58.51% |
| H | 6.24% | 6.20% |
| S | 14.17% | 14.32% |

EXAMPLE 9

Preparation of 2-(5'-isobutyryl-3'-thienyl)propionic acid (VI)

17.71 g (0.0783 mol) of 2-(5'-isobutyryl-3'-thienyl)-propionic acid, 55 ml of diethylene glycol, 12.0 g (0.214 mol) of 85% KOH and 10.5 g (0.201 mol) of hydrazine hydrate are placed in a 250 ml balloon, and a Dean-Stark separator (previously filled with 25 ml of diethylene glycol) is attached to it. The balloon flask is heated in a silicone bath at 140° C. until nitrogen begins to be released. When the nitrogen release is sufficiently constant, the reaction temperature is increased to 200° C., and it is observed that the reaction mixture boils gently, and the water that evolves is collected in the separator. After 8 hours the mixture is cooled and diluted with a large amount of water and acidified. After extraction with ether, a crude product of 14.59 g is obtained, which is distilled at reduced pressure.

Yield: 78%.

Boiling Point = 154°–155° C. at 0.10 torr.

IR (film): 3600–2200, 2960, 1710, 1460, 1215, 910 cm$^{-1}$.

NMR (CD$_3$COCD$_3$): 9.71 s (wide (1) which disappears upon deuteration, 7.00 s (1) H thiophenic, position 2, 6.80 s (1) H thiophenic, position 4, 3.73 c (1) CH$_3$13 CH—COOH, 2.63 d. (2) (CH$_3$)$_2$—CH—CH$_2$—, 1.84 m (1) (CH$_3$)$_2$—CH—CH$_2$—, 1.42 d (3) CH$_3$—CH—COOH, 0.92 d (6) (CH$_3$)$_2$—CH—CH$_2$.

| Elemental Analysis (C$_{11}$H$_{16}$O$_2$S): | | |
|---|---|---|
| | Calculated | Found |
| C | 62.23% | 62.49% |
| H | 7.60% | 7.80% |
| S | 15.10% | 15.40% |

EXAMPLE 10

Preparation of 2-(5'-benzyl-3'-thienyl)propionic acid (VII)

The procedure indicated in Example 9 is followed.
1.70 g (6.54 mmol) of 2-(5'-benzoyl-3'-thienyl)propionic acid
40 ml of diethylene glycol
1.72 g (26.126 mmol) of 85% KOH
1.26 g (26.16 mmol) of hydrazine hydrate.

About 1.5 g crude product is obtained, which is chromatographed on 150 g of SiO$_2$, using a calibrated column, and using a mixture of benzene, ethyl acetate and acetic acid in a ratio of 85:7:8 as eluent. An orange-colored viscous oil is obtained which eventually solidifies.

Yield: 2.04 g (4.23 mmol, 65%).

M.P. = 47°–55° C.

IR (film): 3500–2300, 1715, 1610, 1590, 1560, 1500, 1460, 1285, 1235, 1070, 930, 700 cm$^{-1}$.

NMR (CH$_3$COCD$_3$): 10.12 s (1) wide, vanishes when D$_2$O is added, 7.38 s (5) H benzenic, 7.12 d (1) H thiophenic, position 2, 7.01 d (1) H thiophenic, position 4, 4.10 s (2) H benzylic, 3.81 c (1) H methinic, 1.42 d (3) H methylic.

| Elemental Analysis (C$_{14}$H$_{14}$O$_2$S): | | |
|---|---|---|
| | Calculated | Found |
| C | 68.22% | 68.39% |
| H | 5.73% | 5.78% |
| S | 12.99% | 12.87% |

Most of the compounds described in these examples have been tested pharmacologically and toxicologically (DL$_{50}$) according to the methods indicated on pages 5 to 7, and the results are summarized in the appended table.

| COMPOUND | EXAMPLE | ANTI-INFLAMMATORY ACTION | | ANALGESIC ACTION | | DL$_{50}$ (mouse) |
|---|---|---|---|---|---|---|
| | | Δ volume ED$_{50}$ | Δ abscess ED$_{50}$ | Acetic acid ED$_{50}$ | Plate ED$_{50}$ | |
| LMC-I | 4 | +++ 7.3 mg/kg | +++ 12.5 mg/kg | +++ 50 mg/kg | — | approx. 400 mg/kg |
| LMC-II | 5 | +++ | +++ | +++ | — | approx. |

| COMPOUND | EXAMPLE | ANTI-INFLAMMATORY ACTION | | ANALGESIC ACTION | | DL$_{50}$ (mouse) |
|---|---|---|---|---|---|---|
| | | Δ volume ED$_{50}$ | Δ abscess ED$_{50}$ | Acetic acid ED$_{50}$ | Plate ED$_{50}$ | |
| LMC-III | 6 | 17.3 mg/kg ± | 23.5 mg/kg + | 69.6 mg/kg + | + | 1200 mg/kg approx. |
| LMC-IV | 7 | +++ | ++ | ++ | ++ | 1000 mg/kg approx. |
| LMC-V | 8 | ++ | + | — | + | 1200 mg/kg approx. |
| LMC-VI | 9 | + | + | — | + | 1500 mg/kg greater than 1000 mg/kg |
| LMC-VII | 10 | + | — | — | — | approx. 1500 mg/kg |

+++ = Intense action
++ = Medium action
+ = Minimal action
± = Doubtful action
— = Negative action
— = Not tested As it can be seen from this table, the most active compounds are compounds I and II, whose ED$_{50}$ has also been tested. As for the acute toxicity of these compounds (LD$_{50}$), it is acceptable, being even low in some of them. Their gastric tolerance is normal and acceptable in comparison with that of the majority of the standards employed and of the present-day products.

The administration of these compounds in man is performed orally in the form of gelatin capsules or dragees, rectally by suppositories, and topically in the form of cream or gel.

It will be understood that the specification and examples are illustrative but not limitative of the present invention and that other embodiments within the spirit and scope of the invention will suggest themselves to those skilled in the art.

What is claimed is:

1. 5'-substituted 2(3'-thienyl)propionic acids of the formula

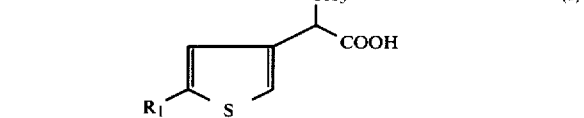

wherein R$_1$ is benzyl or alkanoyl, said alkanoyl group having 1 to 6 carbon atoms.

2. Compounds of claim 1, wherein R$_1$ is benzyl.
3. Compounds of claim 1, wherein R$_1$ is alkanoyl.
4. 2-(5'-benzyl-3'-thienyl)propionic acid.
5. A pharmaceutical composition for treatment of inflammation in animals and in humans comprising an anti-inflammatory amount of a compound of Formula I and a pharmaceutically acceptable carrier.

* * * * *

UNITED STATES PATENT AND TRADEMARK OFFICE
CERTIFICATE OF CORRECTION

PATENT NO. : 4,690,945

DATED : September 1, 1987

INVENTOR(S) : Sabastian J. Arechaga, et al.

It is certified that error appears in the above-identified patent and that said Letters Patent is hereby corrected as shown below:

Column 4, line 57: change "precippitate" to -- precipitate --.

Column 7, line 51: change "0.201" to -- 0.210 --.

Column 8, line 11: change "$CH_3 13CH-COOH$" to -- $CH_3 = CH - COOH$ --.

Column 2, line 14: "2-3'-thienyl)" should be -- 2-(3'-thienyl) --.

Signed and Sealed this

Fourteenth Day of June, 1988

Attest:

DONALD J. QUIGG

Attesting Officer

Commissioner of Patents and Trademarks